United States Patent [19]

Ser et al.

[11] Patent Number: 5,100,674
[45] Date of Patent: Mar. 31, 1992

[54] PROCESS FOR PREPARING AN EFFERVESCENT AQUEOUS SOLUTION HAVING AN EMOLLIENT ACTION ON THE CUTICLE OF THE NAILS, COMPOSITION FOR CARRYING OUT THE SAID PROCESS AND CORRESPONDING COSMETIC TREATMENT

[75] Inventors: Jean-Claude Ser, Chevilly-Larue; Florence Martin, Issy-Les-Moulineaux, both of France

[73] Assignee: L'Oreal, Paris, France

[21] Appl. No.: 592,479

[22] Filed: Oct. 5, 1990

[30] Foreign Application Priority Data

Oct. 13, 1989 [FR] France .................. 89 13421

[51] Int. Cl.$^5$ .................. A61K 7/04; A61K 9/14; A61K 9/46; A61K 31/40
[52] U.S. Cl. .................. 424/466; 424/61; 424/44; 424/717; 424/485; 424/486; 424/487; 424/488; 424/499; 424/500; 424/501
[58] Field of Search ........... 424/466, 61, 44, 499–501, 424/484–488, 717

[56] References Cited

U.S. PATENT DOCUMENTS

| | | | |
|---|---|---|---|
| 4,344,932 | 8/1982 | Gordon | 424/61 |
| 4,530,828 | 7/1985 | Smith et al. | 424/70 |
| 4,533,545 | 8/1985 | Sebag | 424/63 |
| 4,590,069 | 5/1986 | Deckner et al. | 424/61 |
| 4,879,105 | 11/1989 | Yorozu | 424/44 |

*Primary Examiner*—Thurman K. Page
*Assistant Examiner*—E. J. Webman
*Attorney, Agent, or Firm*—Cushman, Darby & Cushman

[57] ABSTRACT

Preparation of an effervescent aqueous solution which has an emollient action on the cuticles of the nails, by dissolving the following anhydrous solid compounds substantially simultaneously in water: urea, pyrrolidonecarboxylic acid and an alkali metal and/or ammonium bicarbonate, and additional ingredients, the different compounds being introduced in the form of a mixture or of several separate mixtures prepared in advance. These mixtures are in pulverulent or tablet form.

Composition for the preparation of the effervescent aqueous solution.

Cosmetic treatment of the cuticle of the nails using the effervescent aqueous solution.

26 Claims, No Drawings

PROCESS FOR PREPARING AN EFFERVESCENT AQUEOUS SOLUTION HAVING AN EMOLLIENT ACTION ON THE CUTICLE OF THE NAILS, COMPOSITION FOR CARRYING OUT THE SAID PROCESS AND CORRESPONDING COSMETIC TREATMENT

The present invention relates to a process for preparing an effervescent aqueous solution having an emollient action on the cuticle of the nails, intended for a cosmetic and/or pharmaceutical treatment; the present invention also relates to a composition for carrying out this process and a process for cosmetic treatment of the nails using the aqueous solution obtained.

Manicure treatments generally include a treatment of the nails to remove the cuticles, that is to say the cornified prolongation of the eponychium covering the nail, therefrom, and thereby to give a better-groomed appearance to the nails. Traditional mechanical treatment is not advisable, since it is considered to be injurious to the nails. To replace this mechanical treatment, compositions presented in the form of solutions, creams or gels, which are brought into contact with the cuticle of the nails and which have the function of softening and partially destroying the cuticle, have been used. However, the compositions proposed hitherto are based on potassium hydroxide, sodium hydroxide or borates, which are strongly alkaline substances and consequently caustic; the compositions used hence attack the nail and the skin of the fingers in proximity to the nail.

Moreover, it is known to use effervescent products in the pharmaceutical and cosmetic field. Effervescent wafer capsules counteracting headaches or effervescent bath salts may be mentioned, for example. In these products, the effervescence is obtained by reaction between a bicarbonate, most often sodium bicarbonate, and an acid RH according to the following reaction scheme:

$$CO_3HNa + R-H \rightarrow CO_2 \uparrow + Na-R + H_2O$$

The fact that the products are effervescent makes them more pleasant and/or more comfortable to use.

The subject of the present invention is an effervescent solution which has an emollient action on the cuticles without attacking the nails and the skin of the fingers in proximity to the nail.

According to the present invention, the use is proposed of an aqueous solution prepared by substantially simultaneous introduction into water of the following anhydrous solid compounds: urea, pyrrolidonecarboxylic acid (PCA) and alkali metal and/or ammonium bicarbonate.

On being introduced into water, urea and the alkali metal or ammonium bicarbonate dissolve. Pyrrolidonecarboxylic acid, which is only sparingly soluble in water, reacts gradually with the alkali metal and/or ammonium bicarbonate in solution to form the alkali metal and/or ammonium salt of pyrrolidonecarboxylic acid, which is soluble in water, with evolution of carbon dioxide. The PCA salt obtained is a hydrating agent, the action of which complements the emollient action of the urea. A solution is thereby obtained which does not attack the nails and the skin of the fingers in proximity to the nail, while having an efficacious emollient action for removing the cuticles. In addition, as a result of the evolution of carbon dioxide, the solution is effervescent, which adds to the comfort on using it.

It may be noted that, according to the present invention, pyrrolidonecarboxylic acid has a dual function: to produce in the solution a salt having a hydrating action and to produce an effervescent solution. Moreover, the complete absence of water in the solid compounds used enables the urea to be stored in the presence of the other products without problems of stability arising.

The subject of the present invention is hence a process for preparing an effervescent aqueous solution having an emollient action on the cuticle of the nails, intended for a cosmetic and/or pharmaceutical treatment, characterized in that anhydrous solid compounds are introduced substantially simultaneously into an aqueous medium on the basis of 1 g to 15 g per 100 g of aqueous medium, in the following proportions referred to 100 parts by weight for the collective anhydrous solid compounds introduced:

10 to 25 parts by weight of urea,
50 to 90 parts by weight of at least one alkali metal and/or ammonium bicarbonate and pyrrolidonecarboxylic acid (PCA), the weight ratio of the bicarbonate(s) to PCA being between 1:4 and 4:1, and
0 to 40 parts by weight of at least one additional water-soluble ingredient selected from the group composed of compounds, other than those mentioned above, having an emollient action, compounds having a pharmaceutical action for the treatment of the nails and cosmetically and/or pharmaceutically acceptable adjuvants.

The aqueous medium used can contain a cosmetic and/or pharmaceutical adjuvant which does not react with any of the anhydrous solid compounds and has virtually no influence over their solubility. The aqueous medium generally contains more than 95% of water. Preferably, water is used as an aqueous medium.

The anhydrous solid compounds are preferably introduced into the aqueous medium in the form of a single mixture or of several partial mixtures prepared beforehand.

The anhydrous solid compounds are preferably introduced into the aqueous medium adopting the following proportions, referred to 100 parts by weight for the collective anhydrous solid compounds introduced:

15 to 20 parts by weight of urea, and
70 to 85 parts by weight of at least one alkali metal and/or ammonium bicarbonate and pyrrolidonecarboxylic acid (PCA).

The weight ratio of the bicarbonate(s) to PCA is preferably between 2:3 and 3:2.

The alkali metal bicarbonate is, in particular, sodium, potassium or lithium bicarbonate.

Among additional ingredients, as (an)other compound(s) having emollient activity, at least one neutral or basic amino acid is/are preferably introduced, on the basis, in particular, of 0.5 to 10% by weight relative to the collective anhydrous solid compounds. Among these amino acids, arginine, lysine, histidine and proline are selected in particular.

Among additional ingredients, as (a) pharmaceutical compound(s), at least one compound selected from water-soluble antifungal, antiseptic and antimicrobial agents, in cationic, anionic or nonionic form, is preferably introduced, the said compound(s) being used, according to its/their acidity or alkalinity, on the basis of 0.1 to 5%, and more especially 2 to 4%, by weight relative to the collective anhydrous solid compounds. Benzalkonium or benzethonium chloride, hexamidine diisethionate, chlorhexidine digluconate and pyridinethione derivatives in acid form, especially 1-hydroxy-2pyridinethione and more especially the pyridinethione derivatives sold under the brand name OMADINE by the company OLIN CHEMICALS, are selected more especially.

It is also possible to introduce, as an additional ingredient, a commonly used, cosmetically and/or pharmaceutically acceptable adjuvant. At least one thickening agent giving a slight viscosity to the effervescent solution obtained is used in particular, on the basis of 0.05 to 3% by weight relative to the collective anhydrous solid compounds introduced. Among thickening agents, cationic and/or nonionic polymers of the cellulose derivative type and instant-swelling gums of the gum tragacanth type may be mentioned in particular.

As explained in greater detail below, as a cosmetically and/or pharmaceutically acceptable adjuvant, at least one compaction binder may also be used, on the basis of 0 to 30% by weight relative to the weight of the collective anhydrous solid compounds introduced.

It is also possible to introduce at least one colouring and/or at least one fragrance, in particular absorbed on one of the solids of the composition.

To prepare the effervescent solution according to the invention, 1 to 10 g of solid compounds is/are preferably introduced per 100 ml of aqueous medium, but this quantity can be higher, the upper limit essentially being dependent on the solubility of the collective anhydrous solid compounds introduced.

The aqueous medium is advantageously at a temperature of between 15° and 40° C. The pH of the effervescent solution obtained is generally between 7 and 10, and more especially between 8.5 and 9.5.

The solid compounds are introduced substantially simultaneously into the aqueous medium. The term "substantially simultaneously" means that the different solid compounds are introduced over a sufficiently short period of time for the different anhydrous solid compounds not to have the time to react with one another or to decompose significantly before all the anhydrous solid compounds are introduced into the aqueous medium. This period of time does not generally exceed 5 minutes.

The second subject of the present invention is a composition of anhydrous solids which is usable for carrying out the process as defined above.

The solid composition for carrying out the process is characterized in that it contains, in the same pack, in the form of a single mixture or of several separate partial mixtures, per 100 parts by weight:
10 to 25 parts by weight of urea,
50 to 90 parts by weight of at least one alkali metal or ammonium bicarbonate and pyrrolidonecarboxylic acid (PCA), the weight ratio of the bicarbonate(s) to PCA being between 1:4 and 4:1, and
0 to 40% by weight of at least one additional water-soluble ingredient selected from the group composed of compounds, other than those mentioned above, having an emollient action, compounds having a pharmaceutical action for the treatment of the nails and cosmetically and/or pharmaceutically acceptable adjuvants.

This composition preferably contains, per 100 parts by weight:
15 to 20 parts by weight of urea, and
70 to 85 parts by weight of at least one alkali metal and/or ammonium bicarbonate and pyrrolidonecarboxylic acid (PCA).

The weight ratio of the bicarbonate(s) to PCA is preferably between 2:3 and 3:2.

This composition contains the additional ingredients defined above. As an emollient agent, it can contain at least one neutral or basic amino acid, present on the basis, in particular, of 0.5 to 10% by weight relative to the weight of the collective anhydrous solid compounds. The compounds having a pharmaceutical action for treatment of the nails are compounds selected from water-soluble antifungal, antiseptic and antimicrobial agents, in cationic, anionic or nonionic form, the said compound(s) being present on the basis of 0.1 to 5% by weight relative to the collective anhydrous solid compounds introduced. The cosmetically and/or pharmaceutically acceptable adjuvants may be selected from the group composed of thickening agents present on the basis of 0.05 to 3% and a compaction binder present on the basis of 0 to 30%, these percentages being taken relative to the weight of the collective anhydrous solid compounds introduced.

In the case where the pack contains the anhydrous solid compounds in the form of several separate partial mixtures, the bicarbonate(s) on the one hand and the PCA on the other hand are contained in two different partial mixtures. The composition is preferably composed of two different partial mixtures. In this case, the urea is advantageously contained in the same partial mixture B as the PCA, and the bicarbonate(s) is/are contained in the other partial mixture A, the additional ingredients of an acidic nature preferable being in the partial mixture B and those having a basic nature in the partial mixture A.

The mixture or mixtures of anhydrous solid compounds of the composition are in pulverulent form or in the form of (a) tablet(s) obtained from a powder by compaction under pressure.

When the composition contains several pulverulent mixtures, it is presented in the form of a pack containing at least two separate parts. The pack is presented, for example, in the form of a box containing at least two plastic sachets, each sachet containing a mixture of anhydrous solid compounds.

In the case where the composition is in the form of (a) tablet(s), each mixture may be presented in the form of several tablets having the same composition. Each mixture may also be presented in the form of a single tablet containing the quantity of the said mixture necessary for al specified quantity of water. For example, in the case of a single mixture, the tablet can weight 1 to 15 g per 100 ml of aqueous medium. In the case of two mixtures, the composition is in the form of two tablets, the first being, for example, prepared from the mixture A defined above and the second from the mixture B defined above, the tablets of mixtures A and B weighing in total, for example, 1 to 10 g when they are to be introduced into 100 ml of aqueous medium.

It is not necessary, as in the case of the pulverulent mixtures, to package the tablets corresponding to different mixtures is different parts of the pack; the fact that the mixtures are in tablet form suffices to separate the different mixtures and to prevent two anhydrous solid compounds which form part of two different mixtures running the risk of reacting with one another during storage under normal humidity conditions.

The tablets are prepared in a known manner, by compaction under pressure in the presence of a compaction binder used in the proportion of 0 to 30%. The compaction binders used are binders generally known in the pharmaceutical industry. Starch, gums, especially gum arabic, and carboxymethylcellulose may be mentioned. A microcrystalline cellulose, for example that sold under the brand name AVICEL by FMC Corp., is used in particular. It is also possible to introduce into the tablets additives generally used for the manufacture of tablets such as fillers or smoothing agents intended for giving a smooth and shiny appearance to the tablets.

The disintegration time of the tablet(s) is preferably less than 5 minutes as a result of the choice of a suitable compaction pressure This pressure is variable and depends on the quantity of binder and on the effervescent outcome sought. It is, in particular, between $2 \times 10^7$ and $2 \times 10^8$ pascals.

A third subject of the present invention is a process for treatment of the nails using the effervescent aqueous solution obtained according to the process of the present invention. According to this treatment process, the cuticle of the nails is brought into contact with the effervescent aqueous solution for a sufficient time to obtain an emollient action.

According to this treatment, the nails are dipped into the effervescent aqueous solution immediately after the introduction of the anhydrous solid compounds into the aqueous medium, and the said solution is left to act for a time of between 1 and 5 minutes.

The treatment has a cosmetic nature, since it forms part of the manicure treatments intended for improving the appearance of the nails.

It has a pharmaceutical nature, inasmuch as, when the solution contains a pharmaceutical agent, it enables diseases to be treated: infections and inflammations of the periphery of the nail or perionyxis; the emollient action of the effervescent aqueous solution enables the pharmaceutical product to act more efficaciously.

For a better understanding of the subject of the invention, several embodiments thereof will now be described by way of examples which are purely illustrative and non-limiting. In the formulations appearing in these examples, the quantities stated represent relative proportions.

EXAMPLE 1

An anhydrous pulverulent composition for removing the cuticles as a pretreatment for a manicure session is prepared, this composition being intended for hydration at the time of use to give an effervescent solution and being formulated as follows:

| | |
|---|---|
| Sodium bicarbonate | 48 g |
| Pyrrolidonecarboxylic acid | 32 g |
| Urea | 17 g |
| Cationic cellulose derivative marketed by the company "UNION CARBIDE" under the name "POLY-QUATERNIUM - 10" | 3 g |
| Fragrance | q.s. |
| Colouring | q.s. |

This compound is packaged in a plastic sachet welded so as to remain protected from atmospheric moisture.

At the time of use, the manicurist places 8 g of powder in a bowl and adds 100 ml of water at 30° C. thereto. An effervescent solution is obtained, in which the person desiring the manicure treatments simultaneously dips the fingers of one hand, and then the fingers of the other hand, for 2 minutes in each instance.

When the cuticle has undergone an efficacious emollient action, it is then possible for the manicurist to perform the subsequent manicure treatments under the best conditions. The fingers are then rinsed.

EXAMPLE 2

An anhydrous pulverulent composition for removing the cuticles is prepared, this composition, intended for hydration at the time of use to give an effervescent solution, being formulated as follows:

| | |
|---|---|
| Sodium bicarbonate | 35 g |
| Pyrrolidonecarboxylic acid | 50 g |
| Urea | 10 g |
| Polyacrylamide marketed by the company "AMERICAN CYANAMID" under the name "GELAMIDE 250" | 1 g |
| L-Arginine | 4 g |
| Fragrance | q.s. |
| Colouring | q.s. |

The manicurist places 3 g of this powder in a bowl and adds 100 ml of water at 30° C. thereto. The treatment of the nails is performed as in Example 1, and yields similar results.

EXAMPLE 3

An anhydrous pulverulent composition for the treatment of perionyxis is prepared, this composition being intended for hydration at the time of use to give rise to an effervescent solution and being formulated as follows:

| | |
|---|---|
| Sodium bicarbonate | 45 g |
| Pyrrolidonecarboxylic acid | 30 g |
| Urea | 20 g |
| Quaternized guar gum, marketed by the company "CELANESE" under the name "JAGUAR C13" | 1 g |
| Benzalkonium chloride | 4 g |
| Fragrance | q.s. |
| Colouring | q.s. |

When placed in water, this powder leads to an effervescent solution possessing treating properties with respect to perionyxis.

To perform the treatment of perionyxis, 5 g of this powder are placed in a bowl and 100 ml of water at 35° C. are added thereto. The finger exhibiting inflammation on the periphery of the nail is dipped into the effervescent solution thereby formed and maintained therein for 4 minutes.

This treatment is employed twice per day for 3 days, leading to a marked reduction in the inflammation.

EXAMPLE 4

A pulverulent composition is prepared in two separate mixtures A and B, which are introduced simultaneously into water at the time of use. The composition contains 50 g of mixture A and 50 g of mixture B.

The mixture A has the following formulation in grams per 100 g of mixture:

| | |
|---|---|
| Sodium bicarbonate | 96 g |
| Polyacrylamide sold by the company "AMERICAN CYANAMID" under | 3.5 g |

-continued

| | |
|---|---|
| the name "GELAMIDE 250" | |
| Fragrance | 0.5 g |

The mixture B has the following formulation in grams per 100 g of mixture:

| | |
|---|---|
| Urea | 30 g |
| Pyrrolidonecarboxylic acid | 63.9 g |
| Polymer marketed by the company "UNION CARBIDE" under the name "POLYMER JR-400" | 6 g |
| Colouring (Colour Index No. 14700) | 0.1 g |

The mixtures are packaged in the same box in two plastic sachets sealed by welding, containing in total 10 g of product, that is to say 5 g of mixture A and 5 g of mixture B.

The manicurist simultaneously dissolves the contents of the two sachets in 100 ml of water at 25° C.

The treatment of the nails is performed as in Example 1, and the results yielded are similar.

EXAMPLE 5

An effervescent tablet is prepared from a mixture of the following ingredients in the proportions stated:

| | |
|---|---|
| Sodium bicarbonate | 36 g |
| Pyrrolidonecarboxylic acid | 26 g |
| Microcrystalline cellulose sold by the company "FMC CORP." under the trade name "AVICEL PH105". | 25 g |
| Urea | 12 g |
| Colouring | q.s. |
| Fragrance | q.s. |
| Arginine | 1 g |

The mixture is compressed, using a compacting machine, at $10^8$ pascals.

Each tablet represents 12 g of the mixture. At the time of use, it is dissolved in 100 ml of water at 30° C.

The treatment of the nails is performed as in Example 1, and the results yielded are similar.

We claim:

1. Process for preparing an effervescent aqueous solution having an emollient action on the cuticle of the nails, intended for human treatment, characterized in that anhydrous solid compounds are introduced substantially simultaneously into an aqueous medium on the basis of 1 g to 15 g per 100 g of aqueous medium, in the following proportions referred to 100 parts by weight for the collective anhydrous solid compounds introduced:

10 to 25 parts by weight of urea,
   50 to 90 parts by weight of at least one alkali metal and/or ammonium bicarbonate and pyrrolidonecarboxylic acid (PCA), the weight ratio of the bicarbonate to PCA being between 1:4 and 4:1, and
   0 to 40 parts by weight of at least one additional water-soluble ingredient selected from the group consisting of compounds, other than those mentioned above, having an emollient action, compounds having a pharmaceutical action for the treatment of the nails and cosmetically and pharmaceutically acceptable adjuvants; said process further including introducing at least one neutral or basis amino acid on the basis of 0.5 to 10% by weight relative to the collective anhydrous solid compounds introduced.

2. Process according to claim 1, characterized in that water is used as an aqueous medium.

3. Process according to claim 1, characterized in that the anhydrous solid compounds are introduced into the aqueous medium in the form of a single mixture or of several partial mixtures prepared beforehand.

4. Process according to claim 1 characterized in that the anhydrous solid compounds are introduced into the aqueous medium adopting the following proportions referred to 100 parts by weight for the collective anhydrous solid compounds introduced:

15 to 20 parts by weight of urea, and
   70 to 85 parts by weight of at least one alkali metal or ammonium bicarbonate and pyrrolidonecarboxylic acid (PCA).

5. Process according to claim 1, characterized in that the weight ratio of the bicarbonate to PCA is between 2:3 and 3:2.

6. Process according to claim 1, characterized in that the amino acid is selected from the group consisting of arginine, lysine, histidine and proline.

7. Process according to claim 1, characterized in that, among additional ingredients, as a compound having a pharmaceutical action, at least one compound selected from water-soluble antifungal, antiseptic and antimicrobial agents, in cationic, anionic or nonionic form, is introduced, the said compound being used on the basis of 0.1 to 5% by weight relative to the collective anhydrous solid compounds introduced.

8. Process according to claim 7, characterized in that the compound having a pharmaceutical action is selected from the group consisting of benzalkonium or benzethonium chloride, hexamidine diisethionate, chlorhexidine digluconate and pyridinethione derivatives in acid form.

9. Process according to claim 1 characterized in that, as an acceptable adjuvant, at least one thickening agent giving a slight viscosity to the effervescent solution obtained is used on the basis of 0.05 to 3% by weight relative to the weight of the collective anhydrous solid compounds introduced, and at least one compaction binder is used on the basis of 0 to 30% by weight relative to the weight of the collective anhydrous solid compounds introduced, and at least one fragrance and/or at least one colouring is used.

10. Process according to claim 1, characterized in that the aqueous medium is at a temperature of between 15° and 40° C.

11. Process for cosmetic treatment of the nails using the effervescent aqueous solution obtained by the process of claim 10, characterized in that the cuticle of the nails is brought into contact with the said solution for a sufficient time to obtain an emollient action.

12. Process according to claim 11, characterized in that the nails are dipped into the solution, and in that the said solution is left to act for at time of between 1 and 5 minutes.

13. Solid composition characterized in that is contains, in the same pack, in the form of a single mixture per 100 parts by weight:

10 to 25 parts by weight of urea,
   50 to 90 parts by weight of at least one alkali metal or ammonium bicarbonate and pyrrolidonecarboxylic acid (PCA), the ratio of the bicarbonate to PCA being between 1:4 and 4:1, 0 to 40 parts of at least one additional water-soluble ingredient selected from the group composed of compounds, other than those mentioned above, having an emollient action, compounds having a pharmaceutical action for the treatment of the nails and an acceptable adjuvants, at least one neutral or basic amino acid on the basis of 0.5 to 10% by weight relative to the collective anhydrous solid compounds introduced.

14. Composition according to claim 13, characterized in that it contains, per 100 parts by weight:
   15 to 20 parts by weight of urea, and
   70 to 85 parts by weight of at least one alkali metal and/or ammonium bicarbonate and pyrrolidonecarboxylic acid (PCA).

15. Composition according to claim 13, characterized in that the weight ratio of the bicarbonate to PCA is between 2:3 and 3:2.

16. Composition according to claim 13, characterized in that, among additional ingredients, the emollient agent is at least one neutral amino acid, present on the basis of 0.5 to 10% by weight relative to the weight of the collective anhydrous solid compounds introduced.

17. Composition according to claim 16, in which the anhydrous solid components are in the form of several separate partial mixtures, characterized in that the bicarbonate on the one hand and the PCA on the other hand are contained in two different partial mixtures.

18. Composition according to claim 17, wherein the urea is contained in the same partial mixture as the PCA and in that the bicarbonate is contained in the other partial mixture, the additional ingredients of an acidic nature being in the partial mixture containing the PCA and those having a basic nature being present in the partial mixture containing the bicarbonate.

19. Composition according to claim 18, characterized in that the mixture of anhydrous solid compounds is/are in pulverulent form.

20. Composition according to claim 19, characterized in that it is presented in the form of a pack containing at least two separate parts.

21. Composition according to claim 18, characterized in that the mixture of anhydrous solid compounds is/are in the form of a tablet obtained from a powder by compaction under pressure.

22. Composition according to claim 21, characterized in that it contains a compaction binder constituting at most 30% by weight relative to the total weight of the composition.

23. Composition according to claim 21, characterized in that the disintegration time of the tablet is less than 5 minutes as a result of the choice of a suitable compaction pressure.

24. Composition according to claim 13, characterized in that, among additional ingredients, the compounds having a pharmaceutical action for treatment of the nails are provided with at least one compound selected from water-soluble antifungal, antiseptic and antimicrobial agents, in cationic, anionic or noionic form, the said being present on the basis of 0.1 to 5% by weight relative to the collective anhydrous solid compounds introduced.

25. Composition according to claim 13, characterized in that said acceptable adjuvants are selected from the group consisting of thickening agents present on the basis of 0.05 to 3% by weight, these percentages being taken relative to the weight of the collective anhydrous solid compounds introduced, fragrances and colourings.

26. Solid composition characterized in that it contains, in the same pack, in the form of several separate partial mixtures, per 100 parts by weight:
   10 to 25 parts by weight of urea,
   50 to 90 parts by weight of at least one alkali metal or ammonium bicarbonate and pyrrolidonecarboxylic acid (PCA), the ratio of the bicarbonate to PCA being between 1:4 and 4:1,
   0 to 40 parts of at least one additional water-soluble ingredient selected from the group composed of compounds, other than those mentioned above, having an emollient action, compounds having a pharmaceutical action for the treatment of the nails and acceptable adjuvants,
   at least one neutral or basic amino acid on the basis of 0.5 to 10% by weight relative to the collective anhydrous solid compounds introduced.

* * * * *